United States Patent [19]

Dabi

[11] Patent Number: 4,992,326
[45] Date of Patent: Feb. 12, 1991

[54] HYDROPHILIC POLYMERS FOR INCORPORATING DEODORANTS IN ABSORBENT STRUCTURES

[75] Inventor: Shmuel Dabi, Highland Park, N.J.

[73] Assignee: NcNeil-PPC, Inc., Milltown, N.J.

[21] Appl. No.: 90,491

[22] Filed: Aug. 28, 1987

[51] Int. Cl.$^5$ .............................................. B32B 5/16
[52] U.S. Cl. .................................. 428/283; 428/402; 428/403; 428/905
[58] Field of Search ............... 604/359, 358, 360, 365, 604/367; 128/155; 428/223, 290, 402, 403, 905, 244

[56] References Cited

U.S. PATENT DOCUMENTS

| | | | |
|---|---|---|---|
| 4,454,191 | 6/1984 | Blücher | 428/244 |
| 4,455,187 | 6/1984 | Blücher | 428/244 |
| 4,746,567 | 5/1988 | Zelter | 428/905 |
| 4,808,466 | 2/1989 | Kotani et al. | 428/905 |
| 4,817,860 | 4/1989 | Shapiro | 428/905 |
| 4,889,755 | 12/1989 | Charlonneau | 428/905 |
| 4,925,517 | 5/1990 | Charlonneau | 428/905 |

FOREIGN PATENT DOCUMENTS 227932 10/1987 Japan .

*Primary Examiner*—James J. Bell

[57] ABSTRACT

There is disclosed the process of incorporating a deodorant powder (of various mechanisms of action) into a hydrophilic, swellable, water-insoluble absorbent crosslinked polymer, which swellable polymer is coated on a thin, flexible, substrate e.g. a non-woven web, a paper tissue, or a water-insensitive film, and the resultant flexible structure which contain the deodorant powders, held in a dust-free stable manner, and their use as one or more components of body fluid absorbent structures such as sanitary napkins.

1 Claim, No Drawings

HYDROPHILIC POLYMERS FOR INCORPORATING DEODORANTS IN ABSORBENT STRUCTURES

This invention relates to the process of incorporating a deodorant powder into a hydrophilic, swellable, water-insoluble absorbent crosslinked polymer, which swellable polymer is coated on a thin, flexible, substrate e.g. a non-woven web, a paper tissue, or a water-insensitive film, and to the resultant flexible structures which contain the deodorant powders, held in a dust-free stable manner, and their use as components of body fluid absorbent structures.

BACKGROUND OF THE INVENTION

The odor associated with body discharges, such as menstrual fluid and urine, can be effectively eliminated or reduced by many active compounds. The reduction in odor can be accomplished through various mechanisms: (1) by the active ingredient attacking and killing the organism which forms the odorous materials (e.g.-,bactericide); (2) by it interfering with the metabolism cycle which leads to the formation of odor (anti-enzyme, e.g., EDTA); (3) by chemical neutralization of the odorous materials (e.g., sodium bicarbonate neutralizes fatty acids); (4) by strong physical adsorption of materials (e.g., activated charcoal). Other mechanisms are also known. The terms "deodorant" and "antiodorant" as used herein interchangeably, are intended to include all such active ingredients, no matter what specific deodorizing mechanism is involved.

Most antiodorant materials are available only in powder form, and as such, are dusty and difficult to incorporate and contain in commercial body fluid absorbent products such as sanitary napkins or diapers. Additionally, good (and sometimes long) contact must be established between the active deodorant compounds and the body fluid, before odor reduction can be realized.

The present invention serves to solve some of these problems by means of a polymeric system which facilitates the incorporation of antiodorant powders into sanitary napkins and other absorbent products and contains them in a dust free manner, while allowing a good contact with the absorbed body fluid. The term "sanitary napkin" as used herein is intended to include all products conventionally used to absorb menstrual fluid or vaginal discharge, which are not tampons, whether referred to as sanitary napkins, panty shields, panty liners or similar or synonymous names.

PRIOR ART

Kimberly-Clark U.S. Pat. No. 4,547,195 describes a sanitary napkin having a malodor counteracting agent added to a batt of absorbent material which is then folded so the antiodorant agent is concentrated near the most absorbent site. Another means to achieve greater utilization of the active ingredient is disclosed in Beghin-Say's WO 8403-631-A, where a juxtaposition of superabsorbent particles and antibacterial agent is claimed. The composition is made by slurrying an insoluble polyelectrolyte (superabsorbent) and antibacterial agent in methanol followed by evaporation. This creates some adhesion between the two substances. However, powders, in general, would not be contained to form a dust-free product, since they are not embedded in the polymer.

The advantage of the present invention over the prior art is that it allows the formation of a dust-free structure by anchoring the active deodorant powder, yet the active ingredient is still efficacious. Another important advantage of the above process is that the powder/water swellable composite can be formed in situ on any substrate, which can then be used in any desired specific location in the final product.

SUMMARY OF THE INVENTION

The present invention is directed to a deodorant powder-containing body fluid absorbent structure comprising a thin, flexible substrate such as a non-woven web or a paper tissue or a water-insensitive film, which substrate is coated with a hydrophilic, water insoluble, water swellable crosslinked polymeric film containing a powdered deodorant immobilized in a dust-free manner by being completely or partially incorporated in said polymeric film coating, and to the components thereof i.e. the coated substrate having the powdered deodorant immobilized in the swellable crosslinked polymeric film coating.

DETAILED DESCRIPTION OF THE INVENTION

The polymeric system of this invention utilizes hydrophilic, water swellable, water insoluble absorbent polymers (i.e. absorbents and superabsorbents) which completely or partially encapsulate the active deodorant powder. The prefered polymers are water soluble, film forming polymers, which are rendered insoluble by crosslinking them. Examples of such polymers include ammonium or alkali metal salts of poly(meth) acrylic acid, polyacrylamide, poly vinyl alcohol, and starch derivatives. These and other usable polymers are described in U.S. Pat. Nos. 3,926,891 (Dow), 4,154,898 (Dow) and 4,645,785 (Personal Products), and in the book "Water Soluble Resins" by R. L. Davidson, Reinhold Publishing Corp., 1962. p. 106, and are well known materials.

Prior to the insolubilization (or crosslinking) step, the active antiodorant powder is dispersed in the polymer solution which is then crosslinked and dried. In many cases the powder-containing polymer solution can be applied onto substrates such as a non-woven web of textile fibers (typically made with polyester fibers) or paper tissue or water-insensitive film e.g. polypropylene and polyethylene film, and then crosslinked in situ to form a thin coating on the substrate of water swellable polymer which contains active antiodorant materials. The uniqueness of this composite is that the dusty deodorant powder is now well contained in a dust-free manner yet is available to perform its deodorizing function upon contact with aqueous fluids e.g. body discharges, which swell the encapsulating polymer. Moreover, the body discharge or other aqueous fluid is immobilized by the absorbent around the active deodorant and is held in intimate contact with the deodorant, thereby maximizing the efficacy of the deodorant.

The choice of the specific hydrophilic polymer to be used is dependent upon the type of active deodorant involved, the desired absorbent composite and the process conditions to be used for making the absorbent structure.

Most preferably, the process used will involve dispersing the active deodorant powder (or deodorant liquid where the deodorant is first dissolved in a solvent) in a water solution of the hydrophilic polymer, adding a crosslinker and then drying and crosslinking (see Example I).

Another prefered process is to first apply a film of the hydrophilic polymer and then spray it with a solution of a crosslinker or a gelling agent crosslinker (see Example II). In this process the active deodorant could be included in either component. The consecutive application of polymer and gelling agent also helps to overcome many compatibility problems between the polymer solution and active ingredient. For example, a water solution of polysodium acrylate would not tolerate even small amounts of active ingredients containing di or tri valent ions, such as calcium, magnesium and aluminum. In this case, layers of polymer and deodorant solution would be applied in a consecutive manner.

Since in the present invention the deodorant is fixed onto the substrate, it is now possible to design even more effective deodorizing absorbent sanitary napkins and other such end product structures. Various deodorants are individually effective against certain causes of odors, but cannot be used together because they would react with each other if they were part of the same substrate coating. However, by separately incorporating such incompatible deodorants onto different substrates, and then using the different deodorant containing thin flexible substrates in layers in the final end product structure, the incompatibility problem can be solved. (see Example III, which shows how this can be done).

The ratio of polymer to active ingredient is determined by the final performance criteria and by the process conditions. The ratios by weight percent range between 5% powder—95% polymer and 80% powder—20% polymer for purposes of the present invention.

Body fluid absorbent structures are usually composed of layers of materials, e.g. many sanitary napkins and disposable diapers have a facing layer, a backing layer and an inside absorbent layer. The deodorant-containing water-swellable polymeric film coated thin-flexible substrate made from non-woven web, paper tissue or water-insensitive film, of the present invention can easily be incorporated in any desired location in the body fluid absorbent structure. For example, where a suitable non-woven web or impervious film already is being used as part of the total sanitary napkin structure, it first can be coated with a hydrophilic water insoluble water-swellable crosslinked polymeric film containing the desired powdered deodorant immobilized in said coating, and then used as before in the sanitary napkin construction. While the actual placement of the coated substrate in the absorbent product structure is not critical to the instant invention, and it can be placed wherever it is wished to have the powdered deodorant available to contact the body fluid as it is absorbed in actual use, preferably it will be placed as close to the body as possible e.g. on the body facing material, or immediately under the body facing layer.

Many commercially available types of sanitary napkins are constructed somewhat similarly to that depicted in U.S. Pat. No. 4,217,901, which has a (1) rectangular absorbent pad (made of any suitable absorbent material e.g. comminuted wood pulp fibers, cotton linters, rayon fiber, cotton staple etc.) as the core, (2) a body fluid impervious barrier (made of polyethylene or polypropylene film) on the undergarment facing side of the absorbent pad, which is provided to preclude absorbed body fluid from striking through and wetting or staining the undergarment, (3) A sheet of tissue paper surrounding the absorbent pad, (4) a body fluid pervious cover (made of any of the commonly used absorbent product covers such as gauze, non-woven material reinforced with adhesive binders etc.) enveloping the tissue paper wrapped absorbent pad and body fluid impervious cover, and (5) an optional adhesive strip on the undergarment facing surface for those products designed to be adhesively attached to the wearers undergarment.

The deodorant-containing substrate of the present invention e.g. the composite made according to Example II, can be used as a layer directly under the facing material in the above types of sanitary napkin construction.

There are many other constructions known for sanitary napkins, panty liners, etc., some omitting the tissue paper (3) above, but most constructions do have an impervious layer (2) and an absorbent pad (1).

The substrates of the present invention can be used in various places in the sanitary napkin, the choice of which would dictate the specific substrate desired, and they can even replace some of the required layers. Thus the water-insensitive film substrate could be used as the impervious layer (2) above, while the tissue paper substrate could replace that of (3) above, or could be used as a separate layer underneath the tissue paper (3), while the non-woven fiber substrate could be underneath the body fluid pervious cover of, (4) above, or be placed on either side of, or even in the inside of, the absorbent pad (1) above.

The substrates useful in the present invention can be made of any materials which can form a thin, flexible web or film. For use in commercial body fluid absorbent structures e.g., sanitary napkins and diapers where cost of raw materials and manufacturing is a serious consideration, examples of suitable substrates would include such non-woven webs as polyester and polypropylene webs, such paper tissue as crepe paper tissue commercially available from Showano Paper Mills, Shawano Falls, Wis., and such impervious films polyethylene and polypropylene films.

The following examples will better illustrate the invention, but are not intended to limit the invention.

EXAMPLE 1

A 100 g/aqueous solution of polyacrylic acid (12.5% solid, Acrysol A-5 from Rohm & Haas) was neutralized to pH=7 with 6 g of 50% sodium hydroxide. Into that neutralized solution, 2 g of activated charcoal (Darco G-60 from ICI) were slurried and 0.2 g of a crosslinker (XAMA-7, Virginia Chemical-Celanese) was added. From the resultant solution, a 10-mil thick film was cast on a polyethylene sheet and dried for 20 minutes at 60° C.

When the cast film coating was wetted with 1% NaCl aqueous solution (simulating a body fluid), it swelled immediately, and the fluid was immobilized around the activated charcoal deodorant.

The specific polymer used in this example can be successfully replaced by polymethacrylate salts and by any other copolymer of (meth) acrylic acid which is water soluble, at least in its salt form.

The specific deodorant, activated charcoal, used in this example can be successfully replaced by other powdered deodorants.

The specific substrate, polyethylene sheet, used in this example can be successfully replaced by other substrates normally used to construct a sanitary napkin e.g. non-woven fibers, absorbent pads, tissue paper, which can then be used in the same way to construct a sanitary napkin containing one or more deodorants.

EXAMPLE 2

A 15% solution of poly (vinyl alcohol) in water (88% hydrolized, 125,000 MW) was prepared. Into 100 g of that solution, 2.5 g of sodium bicarbonate were dissolved. 6 g of the resultant solution was cast into a 10-mil thick film on a silicon-coated release paper. The cast wet film was sprayed with 1.5 g of a 2% aqueous solution of Borax (gelling cross-linker agent). The resultant wet gel was dried to leave a clear film in which sodium bicarbonate was encapsulated. Alternatively, the PVA/bicarbonate solution was coated on a thin polyester web (0.7 oz/sq. yard) and sprayed with borax solution. The weight of the coating was about equal to the weight of the starting web. The coating was applied two different ways so that in one case both sides of the web were coated, and in the other way only one side of the web was coated. This would be placed under the cover of a typical sanitary napkin where the web is coated on one side only, we prefer that the coated sides be away from the body.

A synthetic fluid consisting of isovaleric, butyric and lactic acids in water (simulates a typical rancid odor) was deposited on the aforesaid film. The odor disappeared almost instantaneously.

Another experiment was also conducted to demonstrate the availability of the encapsulated sodium bicarbonate: A 5% solution of lactic acid containing bromophenol blue indicator has a dark red color in pH lower than 5. However, this solution turned blue, immediately after contacting the aforesaid film with it, indicating effective neutralization of the lactic acid by the encapsulated sodium carbonate.

EXAMPLE 3

In this example two incompatible deodorants are separately fixed onto two different substrates, so more effective structures can be designed. One such structure would separate an acid neutralizing material (sodium bicarbonate) from an amine neutralizing material (poly acrylic acid), so that each one would be active against the corresponding odorant, but they would not neutralize each other. Thus, a first layer is prepared by coating the poly vinyl alcohol and sodium bicarbonate solution described in Example 2, on a 0.7 oz./sq. yd. polyester web. The total add-on ratio of powder and PVA to the web is 1:1. A second layer is prepared by coating a 0.7 oz./sq. yd. polyester web with the polyacrylic acid/charcoal composition described in Example I, except that the polyacrylic acid was neutralized to pH=4. The add-on ratio is again 1:1. By leaving most of the carboxylic groups in their acid form, this layer can neutralize immediately ammonia and amine type odors, which are not affected by the top layer. The two layers can be incorporated into a sanitary napkin as a unitized deodorant insert as described above.

What is claimed is:

1. A thin, flexible substrate in the form of a paper tissue or a water insensitive film, coated with a hydrophilic, water-insoluble, water-swellable cross-linked film forming polymeric material containing a powdered deodorant immobilized in a dust-free manner by being completely or partially encapsulated in said polymeric material.

* * * * *